(12) United States Patent
Singh

(10) Patent No.: US 6,462,033 B2
(45) Date of Patent: Oct. 8, 2002

(54) PROCESS FOR MANUFACTURING COMPOSITIONS CONTAINING CIPROFLOXACIN AND HYDROCORTISONE

(75) Inventor: Onkar N. Singh, Arlington, TX (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/906,233

(22) Filed: Jul. 16, 2001

(65) Prior Publication Data

US 2002/0037883 A1 Mar. 28, 2002

Related U.S. Application Data

(60) Provisional application No. 60/220,865, filed on Jul. 26, 2000.

(51) Int. Cl.[7] .................... A61K 31/56; A61K 31/4965; A01N 45/00
(52) U.S. Cl. .................... 514/171; 514/255.03; 424/449
(58) Field of Search ........................... 514/255.03, 171; 424/449

(56) References Cited

U.S. PATENT DOCUMENTS

| 4,844,902 A | 7/1989 | Grohe | 424/449 |
|---|---|---|---|
| 5,540,930 A | 7/1996 | Guy et al. | 424/427 |
| 5,747,061 A | 5/1998 | Amselem et al. | 424/427 |
| 5,843,930 A | 12/1998 | Purwar et al. | 514/171 |

FOREIGN PATENT DOCUMENTS

| EP | 0 661 055 A1 | 7/1995 |
|---|---|---|
| EP | 0 868 919 A2 | 10/1998 |
| ES | 2065846 | 8/1995 |
| WO | WO 96/39146 | 12/1996 |
| WO | 99/47001 | 9/1999 |
| WO | 00/18386 | 4/2000 |
| WO | 00/18387 | 4/2000 |
| WO | 00/18388 | 4/2000 |
| WO | 00/18404 | 4/2000 |

OTHER PUBLICATIONS

Budavari et al., The Merck Index, 12th edition, 1996, monograph 5452, pp. 925–926.*
Naylor et al., Pharmaceutical Research, 1993;10(6):865–870.*
Engel et al., "Effectiveness of Specific Antibiotic/Steroid Combinations for Therapy of Experimental *Pseudomonas aeruginosa* Keratitis," Current Eye Research, pp. 229–234 (1994).
Hobden et al., "Ciprofloxacin and Prednisolone Therapy for Experimental Pseudomonas Keratitis," Current Eye Research, vol. 11(3), pp. 259–266 (1992).
Hobden et al., "Prednisolone Acetate of Prednisolone Phosphate Concurrently Administered With Ciprofloxacin for the Therapy of Experimental *Pseudomonas Aeruginosa* Keratitis," Current Eye Research, vol. 12(5), pp. 469–473 (1993).
"Biamotil–D" Product Insert.
"Steroid and Antibiotic Solutions and Suspensions," Ophthalmic Drug Facts 1999, pp. 121–122 (1999).

* cited by examiner

Primary Examiner—Russell Travers
Assistant Examiner—San-ming Hui
(74) Attorney, Agent, or Firm—Patrick M. Ryan

(57) ABSTRACT

This invention is directed toward a method of preparing a topical composition comprising ciprofloxacin and hydrocortisone. The method involves dispersing hydrocortisone with lecithin for greater than 45 minutes prior to combining hydrocortisone with the balance of the composition.

3 Claims, No Drawings

PROCESS FOR MANUFACTURING COMPOSITIONS CONTAINING CIPROFLOXACIN AND HYDROCORTISONE

This application claims priority to U.S. Provisional Application, Ser. No. 60/220,865, filed Jul. 26, 2000.

BACKGROUND OF THE INVENTION

The present invention relates to topically administrable ophthalmic and otic pharmaceutical compositions. In particular, this invention relates to a process for manufacturing compositions comprising ciprofloxacin, hydrocortisone and lecithin.

DESCRIPTION OF RELATED ART

U.S. Pat. No. 5,843,930 discloses topically administrable ophthalmic and otic compositions comprising (a) ciprofloxacin in aqueous solution in an amount effective for antibacterial action; (b) a non-ionic viscosity augmenter unaffected by pH and ionic level, said viscosity augmenter being present in an amount effective for augmenting the viscosity of the composition to a viscosity greater than that of water, said viscosity augmenter being at least 85% hydrolyzed polyvinyl alcohol; (c) a non-ototoxic preservative present in an amount effective for antibacterial action the preservative being benzyl alcohol; (d) water sufficient to produce an aqueous composition; (e) hydrocortisone in aqueous suspension in an amount effective for anti-inflammatory action; (f) lecithin in an amount effective for enhancing suspension of other constituents in the compositions; and (g) polysorbate ranging from polysorbate 20 to 80 in an amount effective for spreading the preparation on a hydrophobic skin surface to the site of infection or inflammation.

According to the '930 patent, the compositions comprising ciprofloxacin and hydrocortisone contain polyvinyl alcohol in an amount effective for augmenting the viscosity of the composition to a viscosity greater than that of water and suspending other constituents of the composition. To allow a ciprofloxacin preparation to be administered in drops from a medicine dropper and to flow by gravity to and remain or deposit in an effective amount at a selected area, a viscosity-augmenting agent that would also serve to suspend hydrocortisone was desirable. For compatibility with ciprofloxacin hydrochloride solubility, viscosity-augmenting agents were preferably non-ionic and unaffected by pH and ionic level. See Col., 8, lines 13–31 of the '930 patent.

Polyvinyl alcohol was selected for its ability to produce a suitable viscosity and a high ability to suspend hydrocortisone in aqueous preparations. See the '930 patent at Col. 8, lines 32–37. The addition of lecithin to the composition enhanced the efficacy of polyvinyl alcohol in suspending hydrocortisone in aqueous preparations with ciprofloxacin hydrochloride and other components. See the '930 patent at Col. 8, line 64-Col. 9, line 12.

The '930 patent discloses a process for manufacturing compositions containing ciprofloxacin and hydrocortisone in Example 5 at Column 5, lines 27-67. According to this manufacturing process, polyvinyl alcohol, lecithin, benzyl alcohol and acetic acid are sequentially added to prepare a first stock solution. Separately sodium chloride and sodium acetate are dissolved in water to form a second stock solution. A third stock solution is prepared by dissolving polysorbate 20 and dispersing hydrocortisone in water. Finally, ciprofloxacin is either added to the first stock solution or ciprofloxacin is prepared as a fourth stock solution by dissolving ciprofloxacin, acetic acid and sodium acetate to form a ciprofloxacin stock solution. After the first and second stock solutions are combined, the ciprofloxacin stock solution is added to the combined solution. Finally, the third stock solution polysorbate 20 and hydrocortisone is mixed with the remaining batch volume.

A suspension composition's physical stability can be measured by two common methods. First, the resuspendability of a composition can be measured by allowing a homogeneous to remain standing in a cylindrical container for a period of time, then determining the number of inversions of the cylindrical container necessary to resuspend any sediment that form while the composition was standing. Second, the rate of settling can be measured by allowing a homogeneous suspension composition to remain standing for a period of time, then observing the height of sedimentation visible in a sample contained in a cylinder. Larger sedimentation heights indicate less separation with less supernatant liquid. Both measures of physical stability are important. A composition that is very easy to redisperse but that settles too quickly can be difficult to manufacture. Suspension compositions must remain well dispersed during processing and filling operations while commercial supplies are prepared in order to insure uniform products.

SUMMARY OF THE INVENTION

The present invention provides ciprofloxacin and hydrocortisone compositions that have excellent physical stability. The compositions are prepared by dispersing for greater than 45 minutes hydrocortisone with lecithin and optionally a polysorbate surfactant prior to combining hydrocortisone with the remainder of the composition. Among other factors, the present invention is based upon the finding that a specific order of addition of ingredients in compositions containing ciprofloxacin, hydrocortisone, a preservative, a non-ionic surfactant, a buffer, a tonicity agent, lecithin, polyvinyl alcohol and water can provide compositions with excellent physical stability. Compositions prepared by dispersing hydrocortisone with lecithin prior to mixing hydrocortisone with the balance of ingredients in the compositions have superior physical stability compared to those prepared by dispersing hydrocortisone with only a polysorbate surfactant prior to adding the hydrocortisone ingredient to the balance of the composition.

DETAILED DESCRIPTION OF THE INVENTION

Unless otherwise indicated, all ingredient concentrations are listed as percent (w/w).

Ciprofloxacin is present in the compositions of the invention in an amount effective for anti-bacterial action. Such amounts range from about 0.01–1%, preferably from about 0.1–0.5%, and most preferably about 0.2%. Compositions of the present invention also comprise hydrocortisone as an anti-inflammatory agent. Hydrocortisone is present in an amount effective for anti-inflammatory action. Such amount typically ranges from about 0.1–3%, preferably about 0.1–2%, and most preferably about 1%. Particularly for ophthalmic use, small particle sizes are preferred. As used herein, "micronized" hydrocortisone means hydrocortisone particles having an average particle size $\leq 10\ \mu\text{m}$ (based on surface area (dsn)). If the particle size of the hydrocortisone raw material as received from the supplier is unsatisfactory, one or more known sizing techniques, such as ball milling or micronizing, can be used to adjust the particle size into the desired range.

To prevent contamination by microorganisms and provide a reasonable shelf-life, the compositions of the present invention include a preservative. Acceptable preservatives are required to cause no or insignificant ototoxicity, sensitization or irritation of the ear. Additionally, the preservative must be jointly soluble with ciprofloxacin in water over a pH range of approximately pH 3–6. The most preferred preservative is benzyl alcohol, which is typically present in an amount from about 0.1–3%, preferably about 0.1–2%, and most preferably about 0.9%.

A tonicity adjusting agent is preferably contained in an amount sufficient to cause the composition to be approximately isotonic, that is an amount effective to adjust the tonicity of the composition from about 150–800 mOsm, preferably 200–600 mOsm. A preferred tonicity-adjusting agent is sodium chloride.

A buffering agent is desirable for the compositions of the present invention. The preferred buffering system is an acetate buffer comprising acetic acid and sodium acetate. Amounts of sodium acetate and acetic acid effective to buffer the preparation in a pH range of about 4.0–5.3, preferably about 4.4–4.9 and most preferably about 4.7, range from about 0.1–3% of sodium acetate and from about 0.01–10% of acetic acid. Preferably the amount of sodium acetate is from about 0.1–2% and most preferably about 0.6–0.7%. Preferably the amount of sodium acid is about 0.1–5% and most preferably about 0.2–0.3%. Sodium acetate is preferably used in the form of sodium acetate trihydrate and acetic acid is preferably used in the form of glacial acetic acid.

To allow the compositions of the present invention to wet and spread on the skin surface at the site of infection or inflammation in the ear canal, a non-ionic surfactant is desirable. The surfactants known as polysorbates, in particular polysorbates 20 to 80, are preferred. Such polysorbates are commercially available under the tradename Tween from ICI Americas, Inc. Most preferred is polysorbate 20. The amount of polysorbate surfactant contained in the compositions of the present invention generally ranges from about 0.01–2%, preferably about 0.05–1%, and most preferably about 0.1%.

To help maintain or improve the physical stability of the suspension composition of the present invention, lecithin or a lecithin derivative is added. Lecithins from natural/vegetative (e.g., egg or soy lecithin) and synthetic origins are known. The primarily type of lecithin is phosphatidylcholine (PC). Other types of lecithins include phosphatidylglycerol; phosphatidylinositol; sphingomyelin; and phosphatidylethanolamine. Derivatives of lecithin with saturated and unsaturated fatty acid side chains on PC, are also known, including: distearoylphosphatidyl choline; dipalmitoylphosphatidyl choline; and dimirystoylphosphatidyl choline. As used herein, "lecithin" includes such derivatives of lecithin. Preferably, the lecithin ingredient comprises at least 75% PC.

Commercially available grades of soy lecithins include a fully hydrogenated soy lecithin comprising 90% phosphatidylcholine available under the tradename Phospholipon 90H from American Lecithin Company and a soy lecithin comprising 75% phosphatidylcholine available under the tradename Lipoid-S75 from Vernon Walden, Inc. The amount of lecithin contained in the compositions of the present invention depends primarily on the concentration of insoluble ingredients in the compositions. The amount of lecithin in the compositions of the present invention generally ranges from about 0.01–5%, preferably about 0.01–2% and most preferably is about 0.15%.

In addition to the excipients mentioned above, the ciprofloxacin and hydrocortisone compositions of the present invention optionally comprise polyvinyl alcohol as a viscosity-augmenting agent. The polyvinyl alcohol contained in the composition of the present invention should be at least 85% hydrolyzed, with grades ranging from 85% hydrolyzed to 99+% hydrolyzed being suitable. Most preferred is an 88% hydrolyzed grade of polyvinyl alcohol, such as that commercially available as Airvol 205S from Air Products and Chemicals, Inc. The amount of polyvinyl alcohol ingredient in the compositions of the present invention is preferably an amount effective to cause the composition to have a viscosity ranging from about 2–8 cps (when measured at room temperature using a Brookfield Viscometer set at 30 rpm and a CP 42 spindle). Preferably, the polyvinyl alcohol ingredient is present in an amount sufficient to cause the composition's viscosity to be from about 3–7 cps.

The compositions of the present invention are prepared in a specific manner. It is essential that the hydrocortisone ingredient is first mixed with lecithin for greater than 45 minutes prior to combining the hydrocortisone ingredient with the remainder of the composition. Preferably, hydrocortisone is mixed with both lecithin and a polysorbate 20 to 80 surfactant before combining hydrocortisone with the remainder of the composition. The presence of the polysorbate surfactant provides a lower viscosity slurry than simply mixing hydrocortisone and lecithin alone. The lower viscosity achieved by the addition of the polysorbate surfactant makes processing easier.

As mentioned above, hydrocortisone is preferably sized to achieve desirable particle sizes. The hydrocortisone ingredient in the compositions of the present invention can be sized in the presence of lecithin and optionally a polysorbate 20 to 80 surfactant. If the hydrocortisone ingredient is sized prior to mixing with lecithin, then the mixing with lecithin step must occur prior to combining hydrocortisone with the remainder of the ciprofloxacin and hydrocortisone composition. Particle sizing techniques are known in the art and include ball milling, homogenization and micronization. As used herein, "mixing" includes simple mixing as well as sizing procedures.

The lecithin ingredient should be dispersed in water at a temperature above the phase transition temperature for the chosen grade of lecithin. In the case of phospholipon 90H, the phase transition temperature is approximately 51° C. Therefore, Phospholipon 90H is preferably dispersed at a temperature of approximately 65–70° C. A polysorbate surfactant, if present, can be dispersed simultaneously with lecithin or added before or after lecithin is fully dispersed. After the polysorbate surfactant and lecithin are dispersed, hydrocortisone (preferably micronized) is then dispersed. The hydrocortisone is preferably added after removing the lecithin dispersion from heat, but before the lecithin dispersion cools to room temperature. The hydrocortisone ingredient is preferably mixed with the lecithin dispersion for approximately 6 to 18 hours or more, and most preferably about 12 hours, before being added to the remainder of the ciprofloxacin/hydrocortisone composition.

In a separate vessel, ciprofloxacin is dissolved in water with an acetate buffer, then the benzyl alcohol preservative, sodium chloride tonicity adjusting agent and the polyvinyl alcohol viscosity augmenter are sequentially added, with each ingredient being dispersed or dissolved prior to the addition of the next. Although it is possible to add all of these ingredients simultaneously rather than sequentially provided that the vessel contains a sufficient amount of water, sequentially mixing and dispersing is preferred.

After the ciprofloxacin solution has been prepared, it is combined with the hydrocortisone slurry then the pH is adjusted with NaOH or HCl and the batch volume is adjusted with purified water.

The ciprofloxacin/hydrocortisone compositions described above are preferably prepared as follows.

1. Add approx. 5–50% of the total batch volume of purified water to a compounding vessel and heat to a temperature above the transition temperature of the chosen grade of lecithin (in the case of Phospholipon 90H the preferred temperature is approximately 65–70° C.).
2. Using a magnetic stir bar, disperse 50% of the total required amount of lecithin (preferably, Phospholipon 90H) and 50% of the total required amount of surfactant (preferably polysorbate 20) into the heated water of Step 1 until uniformly dispersed (generally about 10–20 min.). Remove from heat.
3. Add the hydrocortisone (preferably micronized hydrocortisone) before the dispersion of Step 2 cools to room temperature and mix for approximately 12 hrs. (i.e., overnight).
4. Prepare a ciprofloxacin solution by adding the following components in order and mix well allowing each to disperse or dissolve before adding the next: the remaining 50% of the total amount of lecithin (at elevated temperature), the remaining 50% of the total amount of surfactant, the preservative, the buffer (e.g., glacial acetic acid then sodium acetate (trihydrate)), ciprofloxacin, and the tonicity-adjusting agent, and optionally polyvinyl alcohol (from stock solution).
5. Prepare a stock solution of polyvinyl alcohol in purified water. The stock solution is preferably prepared at a polyvinyl alcohol concentration of about 0.5 or 1.0% and preferably prepared at 90–95° C. (for easier and faster solution preparation) then cooled to room temperature.
6. Add the hydrocortisone dispersion of Step 3 to the ciprofloxacin solution of Step 4 (while mixing), then mix in the required amount of polyvinyl alcohol stock solution.
7. QS to 90% with purified water
8. Measure and adjust pH to about 4.7 with 1N NaOH and/or 1N HCl, then QS to 100% with purified water.

EXAMPLES

The following examples are presented to illustrate further various aspects of the present invention, but are not intended to limit the scope of the invention in any respect.

The formulations shown in Table 1 were prepared.

TABLE 1

| | FORMULATION # | | | |
|---|---|---|---|---|
| | 1 | 2 | 3 | 4 |
| Ciprofloxacin Hydrochloride, monohydrate | 0.2329* | 0.2329* | 0.2329* | 0.2329* |
| Hydrocortisone, micronized | 1.0 | 1.0 | 1.0 | 1.0 |
| Benzyl Alcohol | 0.9 | 0.9 | 0.9 | 0.9 |
| Polyvinyl Alcohol 99% hydrolyzed (AIRVOL 125) | 2.0 | 0.05 | 0.1 | — |

TABLE 1-continued

| | FORMULATION # | | | |
|---|---|---|---|---|
| | 1 | 2 | 3 | 4 |
| NaCl | 0.9 | 0.9 | 0.9 | 0.9 |
| Sodium Acetate, trihydrate | 0.68 | 0.68 | 0.68 | 0.68 |
| Glacial Acetic Acid | 0.255 | 0.255 | 0.255 | 0.255 |
| Lecithin (Phospholipon 90H) | 0.15 | 0.15 | 0.15 | 0.15 |
| Polysorbate 20 | 0.10 | 0.10 | 0.10 | 0.10 |
| NaOH/HCl | pH 4.7 | pH 4.7 | pH 4.7 | pH 4.7 |
| Purified Water | QS 100 | QS 100 | QS 100 | QS 100 |

*equivalent to 0.2% ciprofloxacin

Formulation #1 was prepared in four pre-mix portions, which were finally combined in a single mixing tank as follows:

a. Polyvinyl alcohol and lecithin are dissolved in purified water, which has been heated to 90–95° C. This solution is cooled to 50° C. before benzyl alcohol is added and dispersed. The solution is cooled to room temperature.
b. Hydrocortisone is dispersed in a mixture of polysorbate 20 and purified water in a second container. The mixture is homogenized to assure uniform distribution of individual particles in the pre-mix.
c. The sodium acetate and glacial acetic acid are dissolved in purified water in a third container, Ciprofloxacin HCl is then added and dissolved in this buffer.
d. Sodium chloride is dissolved in purified water in a fourth container.

The contents of each container are pumped through a polishing filter into the mixing tank in the order given. If necessary, 1N NaOH or 1N HCl is added to adjust pH to 4.7, prior to bringing to final volume.

Formulation #2 was prepared in three different ways.
Formulation #2A was prepared as follows:
Milling Slurry (For a 200 ml formulation batch)

1. Weigh out and add all of the specified amount of hydrocortisone to a 30 ml polypropylene milling bottle.
2. Weigh out and add 50% of the specified amount of 1% Polysorbate 20 stock solution and 50% of the specified amount of lecithin (phospholipon 90H) and heat to approximately 65–70° C. to disperse the lecithin homogeneously.
3. Transfer the solution of polysorbate 20 and phospholipon 90 H mixture to the milling bottle.
4. Weigh out and add 75.0 g of zirconia-Y beads (3 mm) to the milling bottle.
5. Shake well to wet the hydrocortisone powder
6. Ball mill slurry for 18 hours at 55 rpm Vehicle:
1. Tare a compounding vessel containing a stirring bar
2. Weigh and add the specified amount of polyvinyl alcohol stock solution
3. Add purified water to approximately 20% of the total batch volume and heat to approximately 65–70° C.
4. Weigh and add the remaining amount of lecithin (phospholipon) and disperse by simple stirring at 65–70° C.
5. Allow to cool to room temperature with stirring
6. Add the following (in order) with stirring allowing each to dissolve/disperse completely before addition of the next: benzyl alcohol, glacial acetic acid, sodium acetate, ciprofloxacin HCl, sodium chloride 7. Transfer the ball milled slurry of hydrocortisone/lecithin/polysorbate 20 mixture through a suitable sieve into the compounding vessel rinsing the beads well with purified water.
8. Weigh and add the remaining amount of 1% polysorbate 20 to the compounding vessel with stirring.
9. QS to 95% of total batch volume with purified water
10. Check and adjust pH to target pH of 4.7 with 1N sodium hydroxide and/or 1N hydrochloric acid.
11. QS to 100% (200 ml) with purified water and allow to mix well.

Formulation #2B was prepared according to the procedure used to prepare Formulation #2A except that the hydrocortisone slurry was made as follows:

1. Weigh out and add all of the required 1% polysorbate 20 stock solution, add all of the required lecithin (Phospholipon 90H) and heat to approximately 65–70° C. to disperse (with stir bar) the lecithin homogeneously.
2. Add all of the required amount of micronized hydrocortisone and mix the hydrocortisone slurry for 45 minutes using a magnetic stir bar.

The vehicle was prepared according to the procedure used to prepare the vehicle for Formulation #2A except that the polyvinyl alcohol stock solution was added in step 6 (after sodium chloride).

Formulation #2C was prepared according to the procedure used to prepare Formulation #2B except that there is no heating in the preparation of the hydrocortisone slurry. The lecithin is dispersed at room temperature instead of approximately 65–70° C.

A preferred method for making Formulation #2 is provided below:

1. Tare a compounding vessel with stirring bar.
2. Add 50% of total batch weight of purified water to the compounding vessel.
3. Heat the purified water and maintain at approximately 65–70° C.
4. Add 50% of the batch weight of Phospholipon 90H into the compounding vessel containing water at 65–70° C. Maintain the temperature for 10–20 minutes while stirring to make sure a homogenous dispersion of Phospholipon 90H is achieved.
5. Remove from heat and add 50% of the batch weight of polysorbate 20 (1% stock solution) to the Phospholipon 90H aqueous dispersion.
6. Add hydrocortisone powder into the compounding vessel and allow mixing by simple stirring for an overnight period (approx. 12 hours).
7. Add the remaining components of the formula into step 6, allowing each component to mix or dissolve well by stirring: benzyl alcohol, glacial acetic acid, sodium acetate (trihydrate), ciprofloxacin hydrochloride, sodium chloride, remaining Phospholipon 90H, remaining polysorbate 20 and polyvinyl alcohol (Airvol 125) as a stock solution.
8. QS to 90% of the batch weight with purified water.
9. Measure and adjust pH to 4.7 with 1N NaOH or 1N HCl, if necessary.
10. QS to 100% of the batch weight with purified water and stir until homogeneous.

Formulation #3 was prepared in two different ways.
Formulation #3A was prepared using the same procedure used for Formulation #2A.
Formulation #3B was prepared using the same procedure used for Formulation #2B.
Formulation #4 was prepared in eleven different ways.
Formulation #4A was prepared using the same procedure used to prepare Formulation #1:

Part I:
1. Tare a compounding vessel with a stirring bar.
2. Weigh and add the specified amount of lecithin.
3. Add a small amount of purified water so the volume is approximately 25% of the total batch volume.
4. Heat to 9° C.
5. Allow the mixture to cool to room temperature and add the benzyl alcohol
6. Mix until homogeneous.
7. Add the following components allowing each to dissolve before adding the next: glacial acetic acid, sodium acetate, ciprofloxacin and sodium chloride.
8. Mix well.

Part II:
1. In another beaker add the polysorbate 20 and hydrocortisone together and mix well.

Part III:
1. Add Part II into Part I and mix well.
2. QS to 95% with purified water.
3. Measure and adjust pH with 1N NaOH and/or 1N HCl to the target pH of 4.7.
4. QS to 100% of batch volume with purified water.

Formulation #4B was prepared using the following method:
1. Weigh out and add the specified amount of hydrocortisone to a 30 ml polypropylene milling bottle.
2. Weigh out and add 50% of the specified amount of 1% polysorbate 20 stock solution.
3. Weigh out and add 75.0 g of zirconia-Y beads (3 mm) to the milling bottle.
4. Shake well to wet the hydrocortisone powder.
5. Ball mill slurry for 18 hours at 55 rpm.

Vehicle:
1. Tare an appropriate sized compounding vessel containing a stirring bar.
2. Weigh and add the specified amount of lecithin.
3. Add purified water to approximately 20% of the total batch volume.
4. Heat with stirring to 90° C.
5. Allow to cool to room temperature with stirring.
6. Add the following (in order) with stirring allowing each to dissolve/disperse completely before addition of the next: benzyl alcohol, glacial acetic acid, sodium acetate, ciprofloxacin HCl, sodium chloride
7. Transfer the ball milled slurry through a suitable sieve into the compounding vessel rinsing the beads well with purified water.
8. Weigh and add the remaining amount of 1% polysorbate 20 to the compounding vessel with stirring.
9. Check and adjust pH to target pH of 4.7 with 1N sodium hydroxide and/or 1N hydrochloric acid.
10. QS to 100% (200 ml) with purified water and allow to mix well.

Formulation #4C was prepared using the same procedure used for Formulation #4B except that the ball milling time for the hydrocortisone slurry was extended from 18 hrs. to 72 hrs.

Formulation #4D was prepared using the following method:
1. Weigh out and add the specified amount of hydrocortisone to a 30 ml polypropylene milling bottle
2. Weigh out and add 50% of the specified amount of 1% polysorbate 20 stock solution
3. Weigh out and add 50% of the specified amount of sodium chloride
4. Add 75.0 g of zirconia-Y beads (3 mm) to the milling bottle
5. Shake well to wet the hydrocortisone powder
6. Autoclave the slurry for 30–35 minutes at 121° C.
7. Ball mill slurry for 18 hours at 55 rpm Vehicle:
1. Tare an appropriate sized compounding vessel containing a stirring bar.
2. Weigh and add the specified amount of lecithin.
3. Add purified water to approximately 20% of the total batch volume.
4. Heat with stirring to 90° C.
5. Allow to cool to room temperature with stirring.
6. Add the following (in order) with stirring allowing each to dissolve/disperse completely before addition of the next: benzyl alcohol, glacial acetic acid, sodium acetate, ciprofloxacin HCl, remaining 50% of sodium chloride
7. Transfer the ball milled slurry into the compounding vessel through a suitable sieve rinsing the beads well with purified water.
8. Weigh and add the remaining amount of 1% polysorbate 20 to the compounding vessel with stirring.
9. Check and adjust pH to target pH of 4.7 with 1N sodium hydroxide and/or 1N hydrochloric acid.
10. QS to 100% (200 ml) with purified water and allow to mix well.

Formulation #4E was prepared using the following method:
Homogenization Slurry:
1. Weigh out and add the specified amount of hydrocortisone to a 50 ml beaker.
2. Weigh out and add specified amount of 1% polysorbate 20 stock solution.
3. Homogenize the mixture for 30 minutes using a POLYRON homogenizer at setting 6.

Vehicle:
1. Tare an appropriate sized compounding vessel containing a stirring bar.
2. Weigh and add the specified amount of lecithin.
3. Add purified water to approximately 20% of the total batch volume.
4. Heat with stirring to 90° C.
5. Allow to cool to room temperature with stirring.
6. Add the following (in order) with stirring allowing each to dissolve/disperse completely before addition of the next: benzyl alcohol, glacial acetic acid, sodium acetate, ciprofloxacin HCl, sodium chloride
7. Transfer the homogenized slurry into the compounding vessel rinsing the beaker well with purified water.
8. QS to 95% of the total batch volume using purified water.
9. Check and adjust pH to target pH of 4.7 with 1N sodium hydroxide and/or 1N hydrochloric acid.
10. QS to 100% (200 ml) with purified water and allow to mix well.

Formulation #4F was prepared using the same procedure used for Formulation #2A except that the slurry was ball milled for 72 hrs. instead of 18 hrs.

Formulation #4G was prepared using the same procedure used for Formulation #2A.

Formulation #4H was prepared using the same procedure used for Formulation #2A except that no polysorbate 20 was used in the milling slurry. All of the required amount of polysorbate 20 was added in Step 8 of the vehicle preparation.

Formulation #4I was prepared using the same procedure used for Formulation #2B except that the slurry was mixed overnight (approx. 12 hrs.) instead of 45 minutes.

Formulation #4J was prepared using the same procedure used for Formulation #4I except that the hydrocortisone slurry did not contain any polysorbate 20. All of the required amount of polysorbate 20 was added in Step 8 of the vehicle preparation.

Formulation #4K was prepared using the same procedure used for Formulation #2B.

The table below summarizes the differences in the procedures used to make the formulations.

TABLE 2

| Formulation # | Preparation |
| --- | --- |
| 1, 4A | HC + PS20 mixed well |
| 2A, 3A, 4G | HC + 50% of lecithin + 50% of PS20; ball milled for 18 hrs. |
| 2B, 3B, 4K | HC + 100% of lecithin + 100% of PS20; lecithin dispersed at 70° C. by simple mixing for 45 min. |
| 2C | Same as 2B but lecithin dispersed at R.T. |
| 4B | HC + 50% of PS20; ball milled for 18 hrs. |
| 4C | Same as 4B, but ball milled for 72 hrs. |
| 4D | Autoclaving HC + 0.3% NaCl + 50% of PS20, then ball milling for 18 hrs. |
| 4E | HC + PS20 homogenized for 30 min. |
| 4F | Same as 2A, but ball milled for 72 hrs. |
| 4H | HC + 50% of lecithin; ball milled for 18 hrs. |
| 4I | Same as 2B, but mixed ≈12 hrs. |
| 4J | HC + 100% of lecithin; lecithin dispersed at 70° C. by simple mixing for ≈12 hrs. |

The physical stability of suspension formulations is commonly measured in two ways: resuspendability is assessed by measuring the number of inversions (also called strokes) required to redisperse sedimentation which forms after a sample stands undisturbed for a period of time; and rate of settling is assessed by observing the height in millimeters of the column of sedimentation visible in a sample contained in a cylinder after shaking and then standing for a period of time. In order to record the rate of settling results, the following codes are used (in order of increasing turbidity): C: Clear Supernatant Phase, LM: Light Milky Phase (less dense than Homogeneous phase), H: Homogenous Phase (initial homogeneous phase), D: Dense Phase (more dense than Homogeneous Phase), S: Sediment. Larger sedimentation heights indicate less separation with less supernatant liquid and less compaction of sedimentation. The physical stability of Formulations 1–4K was evaluated according to the methods described above and the results are shown in Tables 3 and 4.

TABLE 3

| | FORMULATION # | | | | | |
|---|---|---|---|---|---|---|
| | 1 | 2a | 2B | 2C | 3A | 3B |
| Resuspendability Real Time: # of inversions Accelerated (10 min. @ 500 rpm): | 3 (2 days settling) | 1 (7 days settling) | 1 (4 days settling) | 1 (4 days settling) | 1 (9 days settling) | 3 (4 days settling) |
| # of inversions wrist shaking (sec.) Accelerated (30 min. @ 500 rpm): | 8 <1 | 2 <1, <1 | 2, 3 <1, <1 | 3, 3 <1, <1 | 5, 6 <1, <1 | 2, 2 <1, <1 |
| # of inversions | — | — | 3, 3 | 2, 2 | — | 3, 4 |
| Viscosity (cps) (30 rpm, cp 42 spindle @ 250° C.) | 6.14, 5.90 | 3.16, 3.26 | — | — | — | — |
| Osmolality (mOsm/kb) | 556, 552 | — | 546, 538 | 535, 534 | 540, 530 | 543, 537 |

| | FORMULATION # | | | | | |
|---|---|---|---|---|---|---|
| | 4A | 4B | 4C | 4D | 4E | 4F |
| Resuspendability Real Time: # of inversions Accelerated (10 min. @ 500 rpm): | 1 (15 days settling) | 1 (15 days settling) | 1 (15 days settling) | 1 (15 days settling) | 1 (15 days settling) | 1 (15 days settling) |
| # of inversions wrist shaking (sec.) Accelerated (30 min. @ 500 rpm): | 2, 3 <1, <1 | 1, 2 <1, <1 | — — | 3, 4 <1, <1 | 2, 3 <1, <1 | 4, 4 <1, <1 |
| # of inversions | — | — | — | — | — | — |
| Viscosity (cps) (30 rpm, cp 42 spindle @ 250° C.) | — | — | — | — | — | — |
| Osmolality (mOsm/kb) | 537, 536 | 532, 536 | — | 536, 543 | 534, 532 | 534, 538 |

| | FORMULATION # | | | | |
|---|---|---|---|---|---|
| | 4G | 4H | 4I | 4J | 4K |
| Resuspendability Real Time: # of inversions Accelerated (10 min. @ 500 rpm): | 1 (9 days settling) | 1 (9 days settling) | 1 (2 days settling) | 1 (4 days settling) | 1 (4 days settling) |
| # of inversions wrist shaking (sec.) Accelerated (30 min. @ 500 rpm): | 4, 4 <1, <1 | — — | 1 <1 | 6, 7 <1, <1 | 3, 2 <1, <1 |
| # of inversions | — | — | 1, 2 | 6, 5 | 3, 3 |
| Viscosity (cps) (30 rpm, cp 42 spindle @ 250° C.) | — | — | 3.96, 4.00 | — | — |
| Osmolality (mOsm/kb) | 540, 545 | — | 549, 546 | 543, 557 | 535, 541 |

TABLE 4

| Rate of Settling | | | | | | |
|---|---|---|---|---|---|---|
| | #1 | #2A | #2B | #2C | #3A | #3B |
| Initial | 0–10 ml: H | 0–10 ml: H | 0–10 ml: H | 0–10 ml: H | 0–10 ml: H | 0–10 ml: H |
| 5 minutes | 0–10 | 0–10 | 0–10 | 0–5 | 0–10 | 0–2.5 |

TABLE 4-continued

| Rate of Settling | | | | | |
|---|---|---|---|---|---|
| | ml: H | ml: H | ml: H | ml: D 5–10 ml: LM | ml: H | ml: S 2–10 ml: LM |
| 10 minutes | 0–10 ml: H | 0–10 ml: H | 0–10 ml: H | 0–29 ml: D | 0–10 ml: H | 0–2 ml: S |

TABLE 4-continued

Rate of Settling

| Time | | | | | | |
|---|---|---|---|---|---|---|
| 15 minutes | 0–10 ml: H | 0–10 ml: H | 0–10 ml: H | 2.9–10 ml: LM 0–2.2 ml: D 2.2–10 ml: LM | 0–10 ml: H | 2–10 ml: LM 0–1.8 ml: S 18–10 ml: LM |
| 20 minutes | 0–10 ml: H | 0–10 ml: H | 0–9.9 ml: H 9.9–4 ml: C | 0–2 ml: D 2–10 ml: LM | 0–10 ml: H | 0–1.6 ml: S 1.6–10 ml: LM |
| 30 minutes | 0–10 ml: H | 0–10 ml: H | 0–9.7 ml: H 97–10 ml: C | 0–2 ml: D 2–9.9 ml: LM | 0–10 ml: H | 0–1.6 ml: S 1.6–10 ml: LM |
| 45 minutes | 0–8 ml: D 8–10 ml: LM | 0–10 ml: H* | 0–9.3 ml: H 93–10 ml: C | 0–19 ml: S 19–10 ml: LM | 0–10 ml: H* | 0–1.6 ml: S 1.6–10 ml: LM |
| 1 Hour | 0–5 ml: S 5–8 ml: LM 8–10 ml: C | 0–10 ml: H | 0–9 ml: H 9–10 ml: C | 0–2 ml: S 2–10 ml: LM | 0–10 ml: H | 0–1.7 ml: S 1.7–10 ml: LM |
| 2 Hours | 0–2.5 ml: S 25–10 ml: LM | 0–10 ml: H | 0–68 ml: H 68–1 ml: C | 0–3 ml: S 31–10 ml: LM | 0–10 ml: H | 0–1.7 ml: S 1.7–10 ml: LM |
| 3 Hours | 0–2.4 ml: S 24–10 ml: LM | 0–9.9 ml: H 9.9–10 ml: C | 0–5.2 ml: D 5.2–10 ml: C | 0–28 ml: S 28–10 ml: LM | 0–9.9 ml: H 9.9–10 ml: LM | 0–2 ml: S 2.1–10 ml: LM |
| 4 Hours | 0–23 ml: S 23–10 ml: C | 0–9.9 ml: D 9.9–10 ml: C | 0–4.7 ml: S 4.7–10 ml: C | 0–2.6 ml: S 26–10 ml: LM | 0–9.9 ml: H 9.9–10 ml: C | 0–20 ml: S 2.0–10 ml: LM |
| 5 Hours | 0–2.1 ml: S 21–10 ml: C | 0–9.9 ml: D** 9.9–10 ml: C | 0–4.2 ml: S 4.2–10 ml: C | 0–25 ml: S 25–10 ml: LM | 0–9.9 ml: H** 9.9–10 ml: C | 0–1.9 ml: S 1.9–10 ml: C |
| 1 Day | 0–1.9 ml: S 1.9–10 ml: C | 0–94 ml: S 9.4–10 ml: C | 0–2.3 ml: H 2.3–10 ml: C | 0–2 ml: H 2–10 ml: C | 0–9.4 ml: H 9.4–10 ml: C | 0–1.6 ml: S 1.6–10 ml: C |

| Time | #4A | #4B | #4C | #4D | #4E | #4F |
|---|---|---|---|---|---|---|
| Initial | 0–10 ml: H | 0–10 ml: H | 0–10 ml: H | 0–10 ml: H | 0–10 ml: H | 0–10 ml: H |
| 5 minutes | 0–2 ml: S 2–7 ml: D 7–10 ml: LM | 0–9.7 ml: D 97–10 ml: LM | 0–9.6 ml: D 9.6–10 ml: LM | 0–9.7 ml: D 9.7–10 ml: LM | 0–2 ml: S 2–7 ml: D 7–10 ml: LM | 0–10 ml: H |
| 10 minutes | 0–2 ml: S 2–10 ml: LM | 0–9.4 ml: D 9.4–10 ml: LM | 0–9.5 ml: D 9.5–10 ml: LM | 0–9.4 ml: D 9.4–10 ml: LM | 0–2.2 ml: S 2.2–10 l LM | 0–10 ml: H |
| 15 minutes | 0–1.9 ml: S 19–10 ml: LM | 0–9.4 ml: D 94–10 ml: LM | 0–93 ml: D 93–10 ml: LM | 0–9.4 ml: D 9.4–10 ml: LM | 0–1.9 ml: S 1.9–10 ml: LM | 0.9–9 ml: H 99–10 ml: LM |
| 20 minutes | 0–1.8 ml: S 1.8–10 ml: LM | 0–9.4 ml: D 94–10 ml: LM | 0–93 ml: D 9.3–10 ml: LM | 0–93 ml: D 9.3–10 ml: LM | 0–1.8 ml: S 18–10 ml: LM | 0–9.9 ml: H 9.9–10 ml: LM |
| 30 minutes | 0–1.5 ml: S 1.5–9.6 ml: LM 96–10 ml: C | 0–9.1 ml: D 91–10 ml: LM | 0–9 ml: D 0–9 ml: LM | 0–92 ml: D 9.2–10 ml: LM | 0–1.6 ml: S 1.6–9.8 ml: LM 9.8–10 ml: C | 0–9.9 ml: H 9.9–10 ml: LM |
| 40 minutes | 0–1.5 ml: S 1.5–95 ml: LM | 0–9 ml: D 9–10 ml: LM | 0–8.5 ml: D 85–10 ml: LM | 0–9 ml: D 9–10 ml: LM | 0–15 ml: S 15–97 ml: LM | 0–9.9 ml: H 9.9–10 ml: LM |

Rate of Settling

| Time | | | | | | |
|---|---|---|---|---|---|---|
| 1 hour | 95–10 ml: C 0–15 ml: S 1.5–9.4 ml: LM 94–10 ml: C | 0–86 ml: D 8.6–10 ml: LM | 0–8 ml: D 8–10 ml: LM | 0–85 ml: D 85–10 ml: LM | 0–1.5 ml: S 1.5–9.6 ml: LM | 9.7–10 ml: C 0–9.9 ml: H 9.9–10 ml: LM 9.6–10 ml: C |
| 2 hours | 0–15 ml: S 15–8.6 ml: LM 8.6–10 ml: C | 0–7.5 ml: D 75–10 ml: LM | 0–55 ml: D 5.5–10 ml: LM | 0–7.4 ml: D 7.4–10 ml: LM | 0–1.5 ml: S 1.5–9.1 ml: LM 9.1–10 ml: C | 0–99 ml: H 9.9–10 ml: LM |
| 3 hours | 0–1.7 ml: S 1.7–7.9 ml: H 79–10 ml: C | 0–6.5 ml: D 65–10 ml: LM | 0–5.4 ml: D 5.4–10 ml: H | 0–6.3 ml: D 6.3–10 ml: H | 0–1.5 ml: S 1.5–8.7 ml: LM 8.7–10 ml: C | 0–9.8 ml: H 9.8–10 ml: C |
| 4 hours | 0–1.8 ml: S 1.8–7.3 l: H 7.3–10 ml C | 0–5.5 ml: D 55–10 ml: LM | 0–4.4 ml: D 4.4–10 ml: LM | 0–5.3 ml: D 53–10 ml: MH | 0–1.8 ml: S 1.8–83 ml: LM 8.3–10 ml: C | 0–9.8 ml: H 9.8–10 ml: C |
| 1 Day | 0–25 ml: S 2.5–10 ml: C | 0–27 ml: S 2.7–10 ml: LM | 0–2.5 ml: S 2.5–10 ml: C | 0–2.8 ml: S 28–10 ml: LM | 0–3.3 ml: S 3.3–10 ml: C | 0–8.9 ml: H 89–10 ml: C |

| Time | #4G | #4H | #4I | #4J | #4K |
|---|---|---|---|---|---|
| Initial | 0–10 ml: H | 0–10 ml: H | 0–10 ml: H | 0–10 ml: H | 0–10 ml: H |
| 5 minutes | 0–10 ml: H | 0–10 ml: H | 0–10 ml: H | 0–10 ml: H | 0–27 ml: S 2.7–10 ml: LM |
| 10 minutes | 0–10 ml: H | 0–10 ml: H | 0–10 ml: H | 0–10 ml: H | 0–2 ml: S 2–10 ml: LM |
| 15 minutes | 0–10 ml: H | 0–10 ml: H | 0–10 ml: H | 0–10 ml: H | 0–1.9 ml: S 1.9–10 ml: LM |
| 20 minutes | 0–10 ml: H | 0–10 ml: H | 0–10 ml: H | 0–10 ml: H | 0–1.7 ml: S 1.7–10 ml: LM |
| 30 minutes | 0–10 ml: H | 0–10 ml: H | 0–10 ml: H | 0–10 ml: H | 0–1.6 ml: S 1.6–10 ml: LM |
| 45 minutes | 0–10 ml: H* | 0–10 ml: H* | 0–10 ml: H | 0–10 ml: H | 0–1.7 ml: S 1.7–10 ml: LM |
| 1 Hour | 0–10 ml: H | 0–10 ml: H | 0–10 ml: H | 0–10 ml: H | 0–1.7 ml: S 17–10 ml: LM |
| 2 Hours | 0–10 ml: H | 0–10 ml: H | 0–99 ml: H 99–10 ml: C | 0–99 ml: H 9.9–10 ml: C | 0–21 ml: S 2.1–10 ml: LM |
| 3 Hours | 0–9.8 ml: H 98–10 ml: LM | 0–97 ml: H 97–10 ml: LM | 0–9.9 ml: H 9.9–10 ml: C | 0–9.9 ml: H 9.9–10 ml: C | 0–22 ml: S 22–10 ml: LM |
| 4 Hours | 0–98 ml: H 9.8–10 ml: LM | 0–9.7 ml: H 9.7–10 ml: LM | 0–9.9 ml: H 9.9–10 ml: C | 0–99 ml: H 9.9–10 ml: C | 0–2.1 ml: S 2.1–10 ml: LM |
| 5 Hours | 0–9.8 ml: H | 0–9.7 ml: H | 0–98 ml: H | 0–98 ml: H | 0–2 ml: S |

TABLE 4-continued

| | Rate of Settling | | | | |
|---|---|---|---|---|---|
| 1 Day | 98–10 ml: LM<br>0–95 ml: H<br>95–10 ml: C | 97–10 ml: LM<br>0–8.9 ml: H<br>89–10 ml: C | 98–10 ml: C<br>0–9.0 ml: H<br>9–10 ml: C | 98–10 ml: C<br>0–8.5 ml: H<br>85–10 ml: C | 2–10 ml: C<br>0–1.7 ml: S<br>1.7–10 ml: C |

*40 min.
**6 hrs.

As shown in Table 3, the formulations prepared according to the method of the present invention (Formulation #'s 2A, 3A, 4F, 4G, 4H, 4I and 4J) have resuspendability results approximately equivalent or superior to those prepared by other methods as comparative examples (Formulation #'s 1, 2B, 2C, 3B, 4A, 4B, 4C, 4D, 4E and 4K). As shown in Table 4, the formulations of the present invention have superior rate of settling results compared to the formulations of the comparative examples. See, for example, the data shown in Table 4 after 2 hours (which represents a target manufacturing time period for allowing pumping and filling final product packages with homogeneous suspension formulations); the formulations of the present invention are substantially homogeneous after 2 hours but the formulations of the comparative examples are not.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

I claim:

1. A method of preparing an aqueous suspension composition comprising ciprofloxacin, hydrocortisone, lecithin, and excipients selected from the group consisting of benzyl alcohol; acetate buffer, sodium chloride; surfactants and pH-adjusting agents, wherein the method comprises
   a) dispersing hydrocortisone with lecithin and optionally a polysorbate surfactant in water for greater than 45 minutes to form a hydrocortisone slurry;
   b) preparing a ciprofloxacin composition separate from the hydrocortisone slurry, wherein the ciprofloxacin composition comprises ciprofloxacin, lecithin, and excipients selected from the group consisting of benzyl alcohol, acetate buffer, sodium chloride, surfactants and pH-adjusting agents; and
   c) combining the hydrocortisone slurry prepared in step a) with the ciprofloxacin composition prepared in step b).

2. The method of claim 1 wherein the ciprofloxacin composition further comprises polyvinyl alcohol as a viscosity-enhancing excipient.

3. The method of claim 1 wherein in step a) the hydrocortisone is dispersed with lecithin and a polysorbate surfactant in water for about 6–18 hours to form a hydrocortisone slurry.

* * * * *